United States Patent [19]

Ferree

[11] Patent Number: 4,755,054
[45] Date of Patent: Jul. 5, 1988

[54] MULTICHANNEL, OPTICAL-FIBER-BASED SPECTROMETER

[75] Inventor: Mark B. Ferree, Fullerton, Calif.
[73] Assignee: E-Squared Engineering, Inc., Huntington Beach, Calif.
[21] Appl. No.: 861,413
[22] Filed: May 7, 1986
[51] Int. Cl.[4] ............................................. G01J 3/51
[52] U.S. Cl. .................................... 356/418; 250/227
[58] Field of Search ............... 356/418, 448; 250/226, 250/227

[56] References Cited

U.S. PATENT DOCUMENTS

| | | | |
|---|---|---|---|
| 3,697,185 | 10/1972 | Kassel et al. | 356/410 |
| 3,999,062 | 12/1976 | Demsky et al. | 350/227 |
| 3,999,864 | 12/1976 | Mutter | 356/448 |
| 4,241,738 | 12/1980 | Lubbers et al. | 356/418 X |

FOREIGN PATENT DOCUMENTS

WO8300384  2/1983  World Int. Prop. O. .......... 356/418

OTHER PUBLICATIONS

Jauch "A Portable Rapid Spectrophotometer for Color Studies" J Phys. E. Sci. Instrum., vol. 12, #12, Dec. 1979, pp. 1171–1175.

Primary Examiner—Vincent P. McGraw
Attorney, Agent, or Firm—Bruce L. Birchard

[57] ABSTRACT

An optical-fiber-based spectrometer utilizes a compact, P-C-board-mountable optical multiplexer which permits multiple channels of reference and measurement data from remote and hostile environments to be analyzed in rapid sequence utilizing synchronized computer data-storage and comparison to give rapid-fire answers to the question of the presence or absence of species of interest in a sample or process being analyzed, the relative light level in the reference and data channels being balanced by an optical attenuator having only an air path, attenuation being effected by controlled misalignment of optical fiber ends.

10 Claims, 6 Drawing Sheets

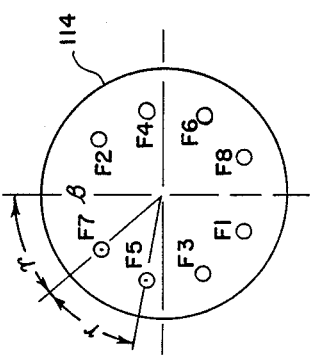
FIG.7a
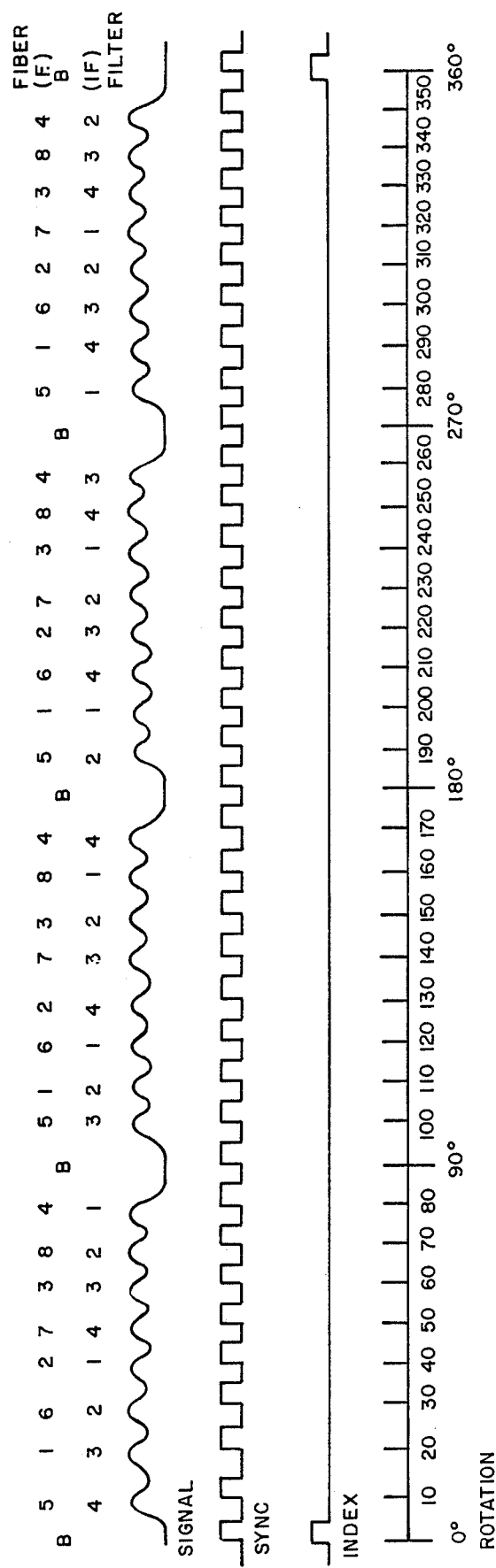
FIG.7b
FIG.8

MULTICHANNEL, OPTICAL-FIBER-BASED SPECTROMETER

BACKGROUND OF THE INVENTION

1. Field of the Invention

This invention relates to spectrometers for use in industrial environments, and more particularly, to such spectrometers wherein on-stream process analysis is possible by means of optical-fiber coupling between remote sensing heads and a multiple channel analyzer located at a distance from the process or products being analyzed.

2. Prior Art

For many years spectrophotometric analyses of processes and products have been effected by the use of instruments in which the infra-red light source, the wavelength changing mechanism, the signal detection and the electronic support equipment were mounted in an enclosure which had to be placed close to the product or process being measured. These devices and systems suffered from certain limitations, for example:

1. The temperatures in the sensing area had to be kept low to prevent damage to the electronics in the sensing head; and,
2. To sense the radiation from two or more areas two or more sensing heads had to be used, which was very expensive; or a traverse mechanism had to be used and that was very complex because of the weight of the sensing head incorporating all the electronics.

These conditions have limited the use and usefulness of spectrometers and, more specifically, spectrophotometers, in industrial environments. It has been clear that industrial processes and product quality control could much more effectively be achieved if spectrometers or spectrophotometers could receive more widespread use in industry. The cost and clumsiness of the equipment, up to this invention, have prevented optimal use of spectrophotometric equipment in industry.

Therefore, it is an object of this invention to overcome the various problems recited for prior art devices and systems.

It is a further object of this invention to provide a low-cost, highly reliable and compact spectrometer which permits multiple channels of analysis of specimens in remote, hostile environments.

SUMMARY OF THE INVENTION

One of the unique features of this on-stream spectrometer (which may be utilized as a process analyzer) is the use of optical-fiber cables to transmit spectral data from simplified, remote sensing heads to a multiple-channel analyzer located at a significant distance from the process or product being analyzed. The spectrometer according to this invention measures the spectral radiance of light signals delivered by multiple optical-fibers, which signals are sampled over discrete optical bands defined by optical band pass filters located in a unique optical bench assembly. By the proper choice of filters and detectors and with the sensor head design described hereinafter, the spectrometer can be used for spectrophotometric applications (transmissive, reflective or scatter), spectroradiometric applications (with calibrated blackbody standardization), fluorescent spectroscopy and colorimetric applications. A spectrometer according to this invention incorporates a novel optical multiplexer which permits multiple channels of reference and measurement data to be analyzed in rapid sequence with appropriate computer data storage and calculation to give rapid-fire answers to the presence or absence of species of interest in a sample or process being analyzed.

BRIEF DESCRIPTION OF THE DRAWINGS

This invention and its mode of operation can best be understood by reading the description which follows in conjunction with the drawings herein, in which:

FIGS. 7a and 7b are schematic mechanical diagrams showing a variation of the configuration of FIGS. 5a and 5b;

FIG. 8 is a timing diagram for the configuration of FIGS. 7a and 7b;

FIG. 9b is a partially cross-sectional view of the component of FIG. 9a.

DETAILED DESCRIPTION OF THE PREFERRED EMBODIMENT

Figure 1:
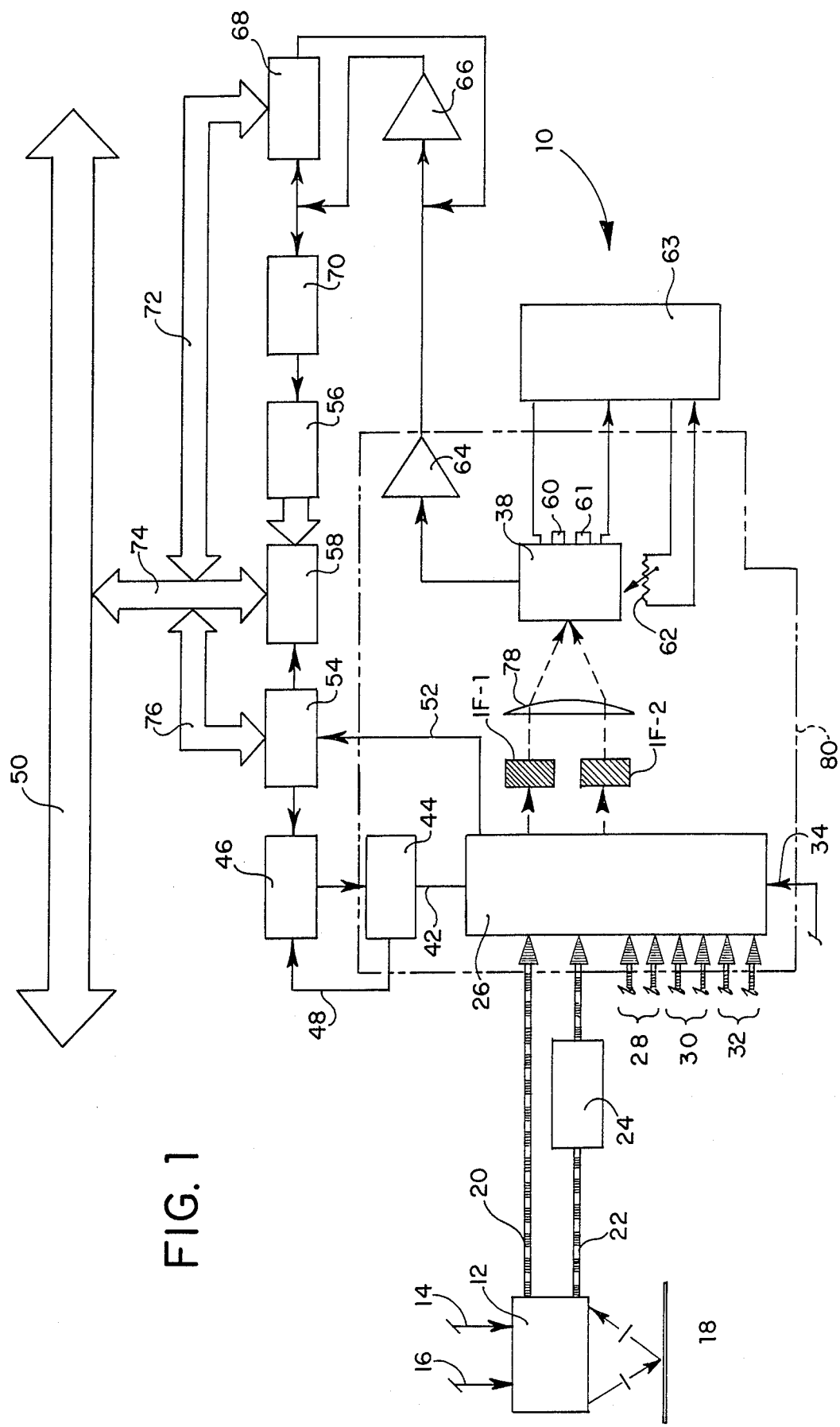
FIG. 1 is a block diagram of a spectrometer according to this invention.

One of the applications for the analyzer or spectrometer according to this invention is as a ratiometric spectrophometer for on-stream composition measurements in the near-infrared (NIR) range from 1 to 2.5 microns. No fundamental vibration absorption bands are found in this region. However, overtones or harmonics and combination absorption may occur as a result of resonances in the mid-infrared (2.4 to 14 micron) range. In an industrial application, for example, it may be desirable to determine the concentration of a single component in a mixture. In such a case two narrow band pass filters may be used: one may be set at a wavelength that is not strongly absorbed by the product being analyzed (background) or by the component of interest and another filter set at a frequency or wavelength that is not as strongly absorbed by the mixture but is strongly absorbed by the component of interest. If the center wavelengths of the filters being used are close enough to each other, the concentration of the component of interest can be roughly approximated by Beers-Lambert Law, as follows:

$$\left. \frac{\partial I}{\partial X} \right|_\lambda = -I(\lambda) \cdot [\alpha(\lambda) C + \sigma(\lambda)]$$

where, $I(\lambda)$≡Spectral radiance intensity of the incident beam.

$\alpha(\lambda)$≡Spectral absorption coefficient of the species of interest.

$\sigma(\lambda)$≡Spectral absorption due to interfering species in the product (background).

C≡Concentration of the species of interest.
X≡Traversing distance of the incident beam
λ≡Wavelength of the incident beam.

To compensate for variations in the incident beam light source, optics and filter response, usually a second signal (through a second optical fiber) is used as a reference—viewing the incident light source but not exposed to the measurement sample absorption. Otherwise, this second "reference" path should be as identical as possible to the first, "measurement" path.

This achieves four signals for each channel. The compound ratios of these signals provide a better, less variant approximation of Beers-Lambert Law. The concentration can be calculated as:

$$C = \frac{\ln\left[K\frac{M_B}{M_A} \cdot \frac{R_A}{R_B}\right] - (\sigma_A - \sigma_B)}{NL(\alpha_A - \alpha_B)}$$

where,
$M_A$, $M_B$≡Intensity of the measurement signals at wavelengths A and B, respectively.
$R_A$, $R_B$≡Intensity of the reference signals.
$\alpha_A, \alpha_B$≡Absorption coefficient of the species of interest.
$\sigma_A$, $\sigma_B$≡Absorption due to interfering species.
C≡Concentration of the species of interest
N≡Units conversion factor.
L≡Total pathlength of the measurement sample.
K≡Correction coefficient for spectral differences in optical efficiencies.

When the interfering components vary in concentration and absorb significantly at the chosen wavelengths, additional filters can be added to account for the variations due to such interfering components. It should also be noted that most detectors are not perfectly linear in their response. If large dynamic ranges are required, a second-order curve-fit of intensity versus detector output is required. The spectrophotometer described herewith can accomplish all of the necessary accommodations.

Figure 2:
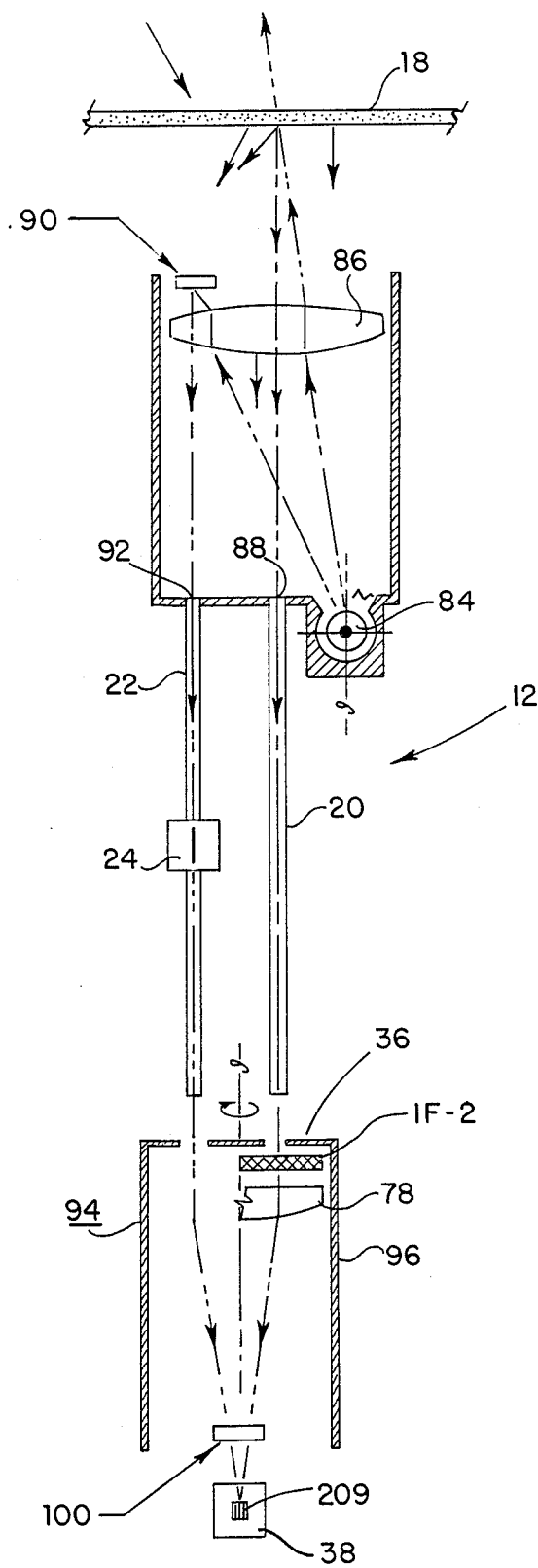
FIG. 2 is a schematic opto-mechanical diagram of one element of the spectrometer of FIG. 1.

In FIG. 1 spectrophotometer or analyzer 10 includes sensing head 12, the details of which are set forth more clearly in FIG. 2. Fundamentally, sensing head 12 is a reflectance measuring head utilizing a tungsten-halogen lamp which radiates a broadband light having frequencies from the visible range to the far infrared range. Power, for the operation of the lamp is provided by way of input lead 14. Purging air may be provided, if desired, by way of tubing 16. Light from the sensing head strikes the product 18 and is reflected back into the sensing head for further processing, as is described in connection with FIG. 2.

Sensing head 12 has two light output channels one coupled to optical-fiber 20 and the other coupled to optical-fiber 22. Optical-fiber 20 carries the light reflected from product 18 and optical-fiber 22 carries a reference light which is generated by reflecting a portion of the output light from the internal lamp into optical-fiber 22. Because the light signal flowing in optical-fiber 22 is much stronger than that flowing in optical-fiber 20, optical attenuator 24 is necessary before the reference signal is fed in to the optical multiplexer 26 along with the measurement or specimen signal carried by optical-fiber 20. The pair of signals assures that any environmental conditions in the sensing head will be cancelled out in the process, leaving only the spectral signal corresponding to the characteristics of the product being analyzed. Three other pairs of specimen and reference signals 28, 30 and 32 may also be introduced into optical multiplexer 26 to provide for semi-simultaneous analyses of multiple products or operating environments. Blanking input 34 represents the space designated "B" on the stationary fiber termination assembly shown in FIG. 5a at which location (as can be seen from considering FIGS. 5a and 5b, together) none of the fiber ends F-1 thru F-8 is aligned with either filter IF-1 or IF-2 of rotating filter mask 36. At that time no light is falling on detector 38 and the dark current of that detector can thus be determined so that the output signal from detector 38, as the result of reference and specimen signals impinging upon detector 38, may be determined with accuracy.

Figure 4:
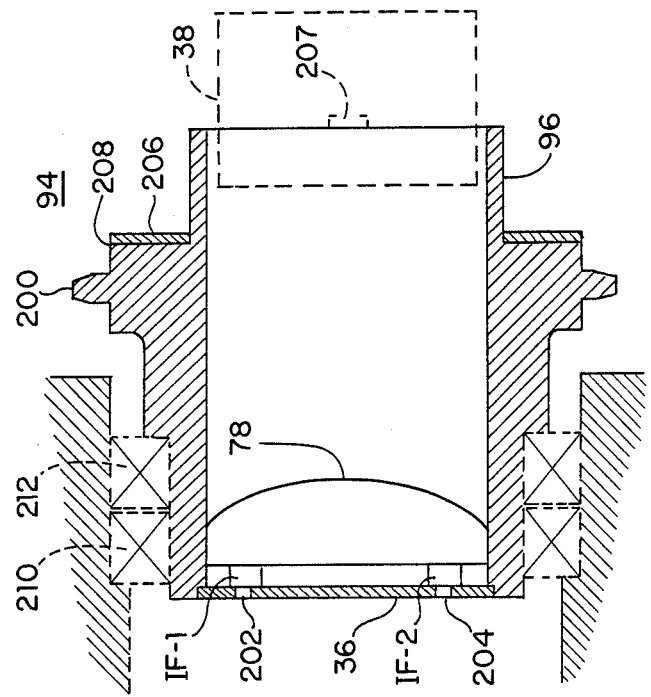
FIG. 4 is a cross-sectional view taken along line 4—4 in FIG. 3.
Figure 5B:
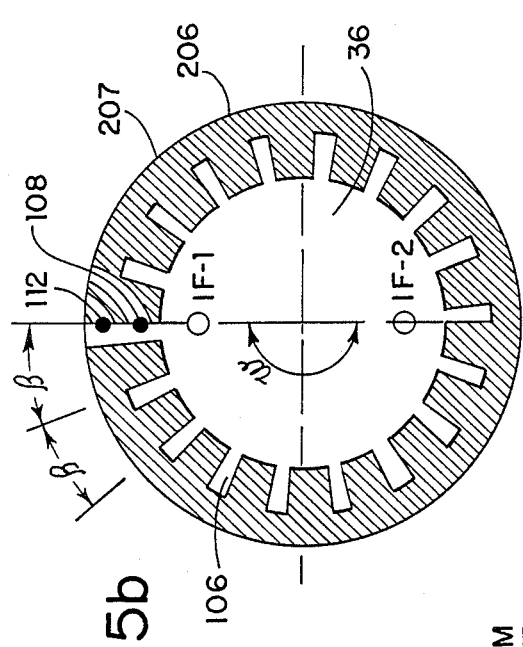
FIGS. 5a and 5b are schematic mechanical diagrams of interacting elements within the spectrometer of FIG. 1.
Figure 5A:
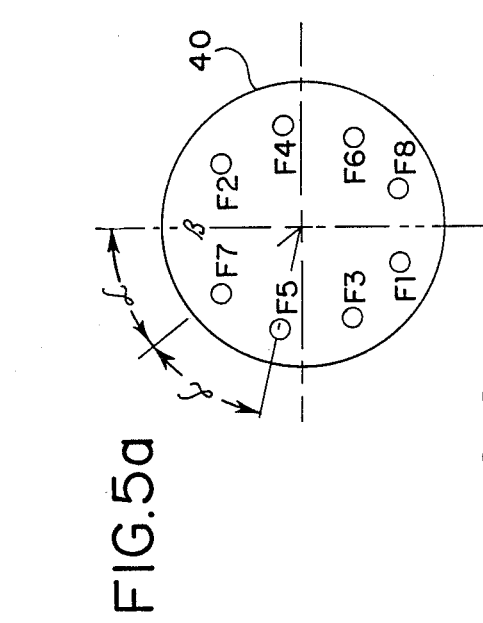

Optical multiplexer 26 includes a motor-driven thin metal disk 36 (FIGS. 3 and 4) carrying two or more filters IF-1, IF-2 which sequentially become aligned with the ends of fibers F-1 thru F-8 in the fiber termination assembly 40 which can be seen more clearly in FIGS. 5a and 7a. As has been said, disk 36 is driven by way of belt drive 42 from motor 44 which may be a brushless D.C. motor. The motor may have a 4-phase, double H-bridge stator and a Samarium-Cobalt magnetic rotor. The advantages of this type of motor over other motors is its high efficiency, high speed, small size and lower susceptibility to magnetic cogging and stalling. The motor is supplied with two Hall-effect sensors (not shown) to provide commutation for the motor-drive electronics. The motor is mounted directly on the optical bench housing and is adjustable to take up the slack in the drive belt 42.

Motor 44 is driven from motor-drive electronics 46. The two Hall-effect sensor signals carried by the connector 48 from motor 44 to motor-drive electronics 46 are decoded to provide four phases of drive power. Motor-drive electronics 46 utilizes in its output stage, output power transistors which are directly heat-sinked to the frame of the optical bench 80 in which optical multiplexer 26 is a crucial part. The microprocessor associated with VME bus 50 can start or stop motor 44 by writing to the status register of the input card carrying optical multiplexer 26.

The motor 44 is driven "open loop", i.e., the speed of the motor is set by the moment of inertia of optical multiplexer 26. The chopping frequency is not critical and can vary plus or minus 100 RPM's with little or no adverse affect. As will be described more fully in connection with FIGS. 4, 5, 5b, 7a and 7b, the rotating element in optical multiplexer 26 carries means for generating both synchronizing and indexing signals which are fed by way of connector 52 to access controller 54.

As has been indicated, access controller 54 receives the synchronization and indexing signals from optical multiplexer 26 by way of connector 52 and causes the data received from A/D converter 56 to be stored in the appropriate location of memory. Access controller 54, before it enables memory 58 to accept data, checks any demands for memory access deriving from the system microprocessor represented by VME-bus 50. Conventional microprocessor techniques are utilized for accomplishing these effects and need not be described extensively here.

Detector 38 is thermoelectrically cooled by way of cooling elements 60, 61 the temperature being sensed by means of thermistor 62 and controlled in controller 63. The output signal from detector 38 is fed thru pre-amp 64 to variable gain amplifier/attenuator 66 which includes a digital-to-analog converter 68 with which there is associated a sample-and-hold circuit 70. Only the peak signals, corresponding to the maximum optimal measurements, are converted and stored.

The variable gain amplifier/attenuator (VGAA) 66 permits the system microprocessor represented by VME bus 50, to set the gain of the amplifier. The gain can be determined as:

$$A_V = G \frac{4095 - N}{N} \text{ or } N = \frac{4095\, G}{A_V + G}$$

where,
$A_v$=Total voltage gain
G=Gain constant
N=Digital word in the DAC (From all zeros=0 to all ones=4095)

It should be noted that the digital word, N=0 is not allowed in this system since such a word would cause the amplifier 66 to saturate at either plus or minus Vcc depending on the sign of the input. With the digital word, N=4095, the VGAA 66 can be shut off with 0 output. The gain constant is not necessarily set to 1, it should be set to the nominal gain required for the application underway. By that technique, the gain can be changed in small steps, either up or down, around the nomimal gain. Although the VGAA 66 can amplify or attenuate, it is normally operated with a net amplification. The system's microprocessor will occasionally download the digital word into the digital-to-analog converter 68 to maintain the highest incoming signal near 95%, thereby maximizing the dynamic range of the analog-to-digital converter 56. Elements 72, 74 and 76 represent busses carrying digital data.

As will be explained in connection with FIGS. 5a, 5b, 7a and 7b filters IF-1 and IF-2 are sequentially aligned with the ends of optical fibers carrying sample signals and reference signals from the samples being tested. Filters IF-1 and IF-2 are very-narrow-band interference filters the light output from which is bent slightly by plano-convex lens 78 so that the light signals from those filters are sequentially directed to the detector 38. All signals are detector the problems of variations in characteristics of various detectors in a multichannel system are eliminated. Filters IF-1 and IF-2 and lens 78 are integral with the rotating disk 36 in optical multiplexer 26. Optical bench 80, which includes optical multiplexer 26, detector 38, preamplifier 64 and motor 44 is sufficiently miniaturized to allow it to be directly mounted onto a printed circuit board for compactness and ease of handling.

Turning to FIG. 2, sensing head 12 includes a tungsten-halogen lamp 84 which radiates a broadband light from the visible to the far infrared. The light from lamp 84 is collimated by lens 86. The light then passes out of sensing head 12 and strikes the sample 18 being analyzed. Sample 18 is located from 2-9 inches away from sensing head 12, for example. Typically sample 18 diffuses the light. What is reflected back into sensing head 12 passes, again, thru collimating lens 86 and impinges upon one end 88 of optical-fiber 20. At the same time, a small mirror 90 reflects a portion of the light output from lamp 84 and such light passes thru lens 86 into end 92 of reference signal optical-fiber 22. The optical path of the sample and reference signals is substantially identical. Because the full spectrum of light from lamp or source 84 irradiates the product or sample 18, this analyzer or spectrophotometer is less susceptible to ambient or stray light, that also impinges on sample 18, than are other pre-filtered light source designs. Since the full spectrum is emitted, non-linear, third order optical effects (e.g., Raman scatterings) can induce some error but these effects are many orders of magnitude less than the Rayleigh resonant scatterings. An advantage of not filtering the light from source 84 before it impinges upon sample 18 is that the filters which are used can be changed more conveniently without disturbing the sensing head which often is in a hostile environment. Sensing head 12 also provides for introduction of purging air to keep lens 86 clear and to add additional cooling.

In ratiometric applications, the magnitude of the reference signal in optical-fiber 22 is often many times greater than the magnitude of the sample signal in optical-fiber 20. If the reference signal in optical-fiber 22 is not attenuated, the dynamic range of detector 38 and its associated electronics is impaired. In such applications it is advisable to attenuate the reference signal by means of optical attenuator 24 in the reference fiber-optic channel. Attenuator 24 is basically a coupling with two eccentric connectors for the optical fibers. When the fiber segments are connected to the coupling, the coupling can be rotated producing a misalignment of the optical fiber cores. Therefore, it is adjustable from the minimum insertion loss of a normal optical-fiber connector, to full cut-off.

The output of optical-fibers 20 and 22 is coupled into optical multiplexer 26 by way of chopper/filter 94 which has cylindrical housing 96, at one end of which is rotating disk 36 which rotates with housing 96. As has been described, rotating disk 36 carries two or more filters such as IF-2 and associated lens 78 which collimates the signal from the optical fibers and directs it thru window 100 onto element 209 in detector 38.

Figure 3:
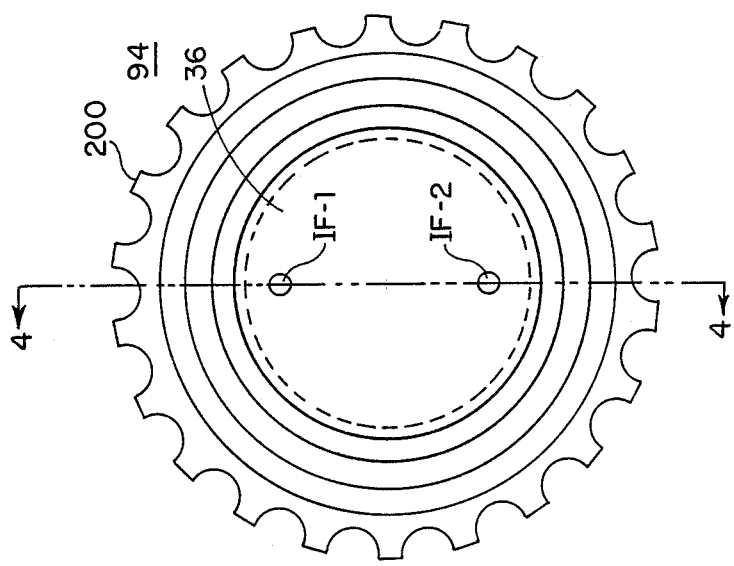
FIG. 3 is a front elevational view of one element in the spectrometer of FIG. 1.

In FIGS. 3 and 4, chopper/filter assembly 94 includes cylindrical housing 96 supported for rotation about its axis in bearings 210 and 212. Sprocket 200 permits driving of housing 96 by a cogged belt and motor, not shown. Housing 96 carries disk 36 at one end thereof so as to cause disk 36 to rotate with housing 96. Disk 36 has a pair of diametrically opposed apertures 202 and 204 therein behind which are filters IF-1 and IF-2, respectively. Disk 36 also carries plano-convex lens 78 which bends the output light beams from filters 202 and 204, respectively, so as to cause those beams to fall on detecting element 207 in detector 38. Cylindrical housing 96 carries on its surface 208 a commutator ring 206 so as to cause that ring to rotate with housing 96 and disk 36. Ring 206 carries reflective strips 106 (FIG. 5b) on a dead-black background to effect chopping of incident light from an LED light source described in connection with FIG. 5b. Synchronizing and indexing pulses are thus generated.

Figure 6:
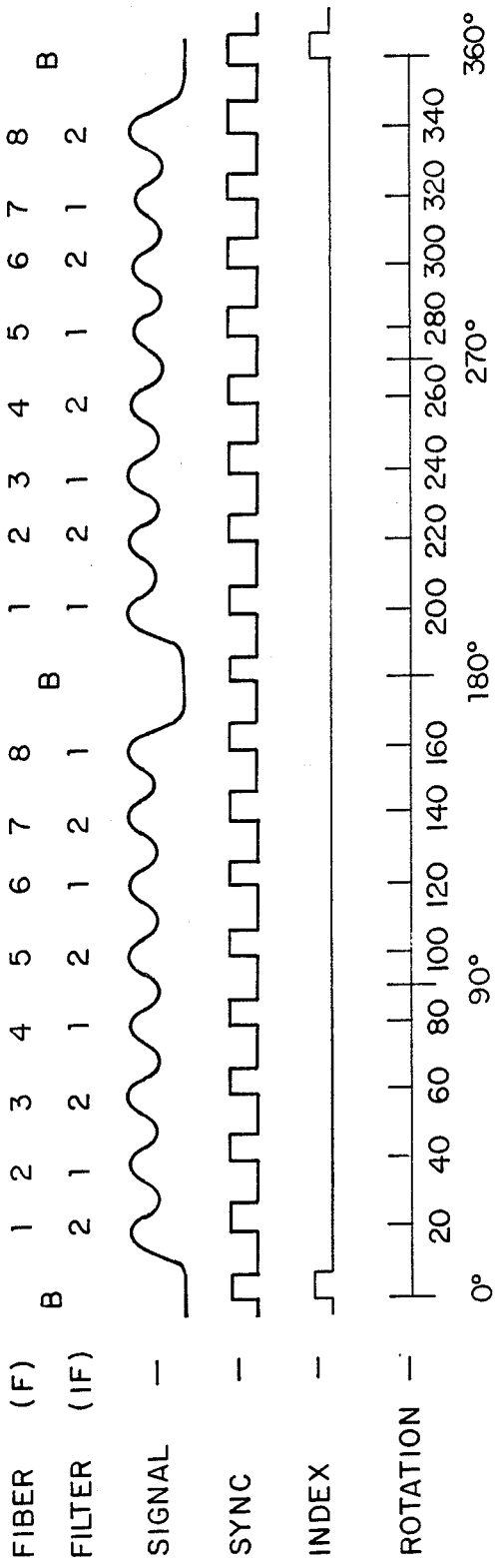
FIG. 6 is a signal timing diagram for the configuration of FIGS. 5a and 5b.

FIGS. 5a, 5b show one possible embodiment of commutator 206 for a nine by two optical multiplexer and FIG. 4 shows the timing diagram for that multiplexer. Eight optical fibers, F1–F8 and a blank position B in FIG. 5a make up the nine inputs. The two filters IF-1 and IF-2 in FIG. 5b, each having a different wavelength of response from the other, provide the two outputs from the multiplexer. FIG. 7b shows a possible configuration for a nine by four optical multiplexer. It should be noted the commutator 206 in FIG. 5b or the commutator disk 214 in FIG. 7b can be shifted a few degrees clockwise or counterclockwise to optimize the position of the synchronizing pulses at the time of maximum signal strength thru the filters. It should also be noted that the assemblies of FIGS. 5a, 5b, 7a and 7b provide the commutators 206 and 214, respectively, each with reflective areas 106 (which may be aluminized) for producing synchronization signals by way of LED/phototransistor combinations 108 and 110, respectively. Light signals emitted by the LED's in these combinations are reflected off of the reflective strips carried by the respective commutators and are picked up by the phototransistor or photodiode included in the combination to produce an output signal each time a reflecting strip passes a combination 108 or 110. Similarly, indexing signals are produced by the LED/phototransistor combination 112 or 114, respectively. Regions 207 on commutator 206 and 213 on commutator 214 are opaque, flat black to aid pulse generation. As can be seen from the FIGS. 5 thru 7 only one fiber and a filter are aligned at any one moment. All signals are measured thru each of the filters once every revolution of disk 36 or disk 216. It should be noted that in the nine by two optical multiplexer of FIGS. 5a and 5b, reflective strips 106 are spaced 20 degrees, that is B=20 degrees whereas in the nine by four optical multiplexer of FIG. 7b these synchronizing strips 106 are, necessarily, spaced only 10 degrees. That is the angle B is 10 degrees. At the same time, the spacing of fiber ends F1 thru F8 is 40 degrees in both the nine by two optical multiplexer and the nine by four optical multiplexer. That is, the angle $\alpha$ in FIG. 5a is 40 degrees and the angle $\gamma$ in FIG. 7a is also 40 degrees. As can be seen from FIG. 6, in the first 180 degree rotation of disk 36, fibers F1, F3, F5 and F7 are first aligned with filter IF-2 and fibers F2, F4, F6 and F8 are first aligned with filter IF-1. In the next 180 degrees of rotation fibers F1, F3, F5 and F7 are aligned with filter IF-1 and fibers F2, F4, F6 and F8 are aligned with filter IF-2. A blanking interval B occurs every 180 degrees because at that time no fiber is aligned with any filter. In the nine by two configuration of FIGS. 5 and 6 a synchronization pulse is generated every 20 degrees and an indexing signal is generated every 360 degrees, after each optical fiber has had the opportunity to be aligned with each of the filters in rotating disk 36. For a brief review it should be noted that fiber termination assembly 40 is fixed in position as are synchronization signal and indexing signal combinations 108 and 112. Disk 36 rotates with cylindrical housing 96. Housing 96 carries reflective elements 106 thereon spaced 20 degrees apart. Filter lens combinations IF-1 and IF-2 are spaced 180 degrees apart and rotate with disk 36.

In FIGS. 7 and 8, four filters, IF-1 thru IF-4 are carried by rotating disk 214 and reflective strips 106 are spaced only 10 degrees. Indexing still occurs only once every full revolution. Again, fiber termination assembly 114 is stationary, as are LED/phototransistor combinations 110 and 114 which generate synchronization and indexing pulses, respectively. The nine by four configuration of FIGS. 7 and 8 permits a more extensive analysis of a sample.

It should be noted that, mechanically, the optical bench 80 is made up of a housing, a frame, a fiber termination assembly, cover plates and the necessary adjustment screws and hardware, not shown.

Figure 9A:
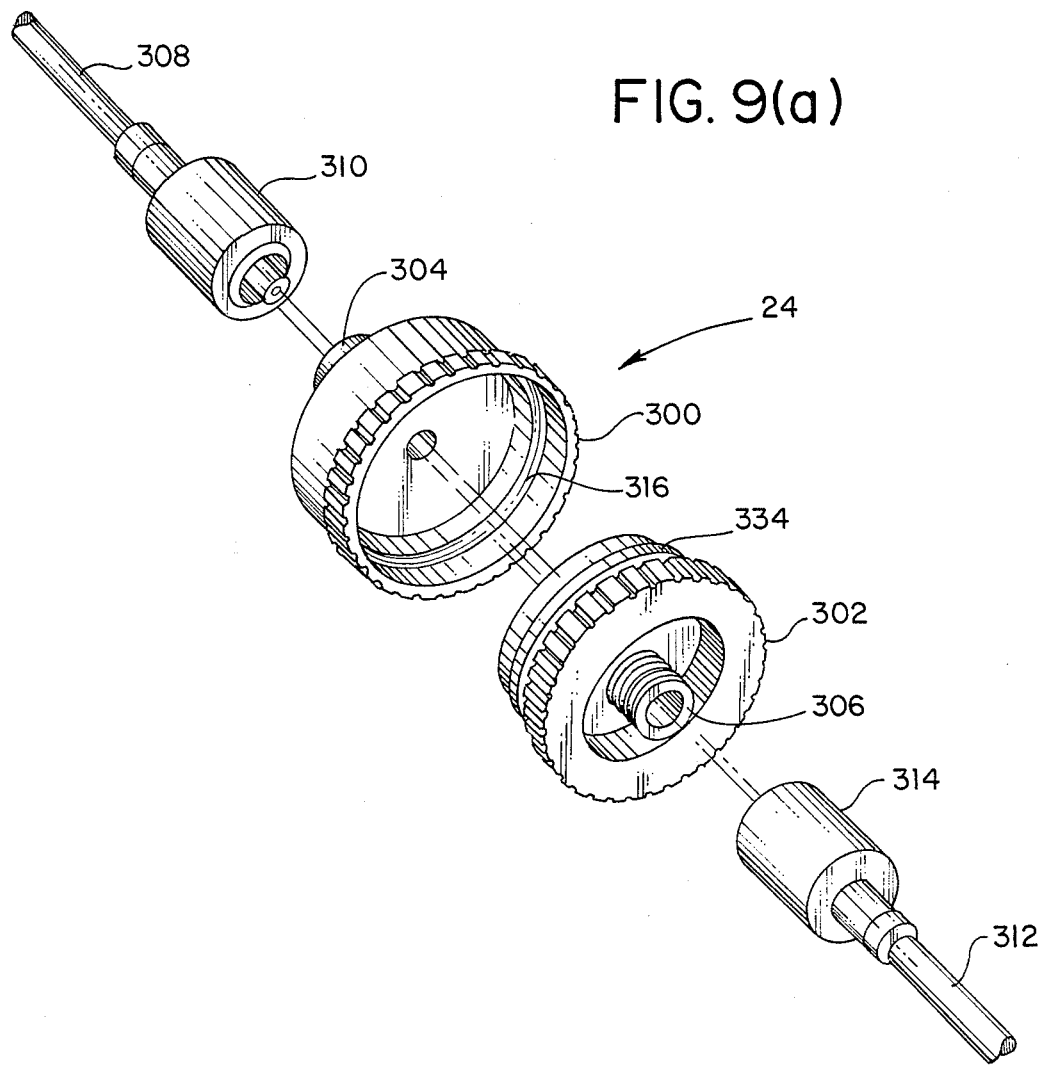
FIG. 9a is an exploded view of one component of of this invention.
Figure 9B:
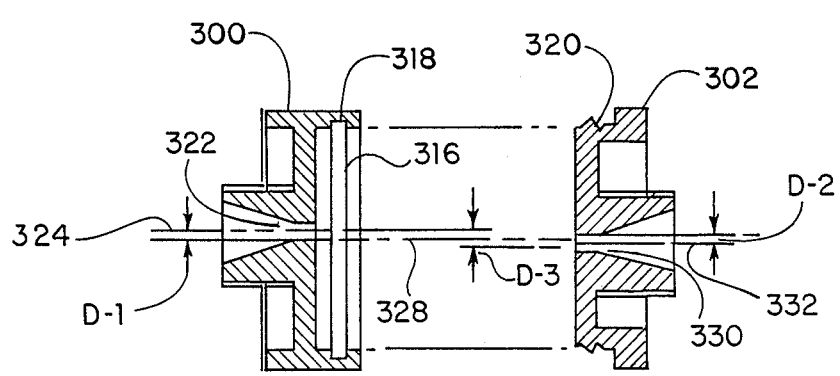

In FIGS. 9a and 9b, optical attenuator 24 includes input shell 300 and output shell 302. Input shell 300 includes threaded input connector 304 and output shell 302 includes threaded output connector 306. Incoming optical fiber 308 terminates in coupler 310 and output optical fiber 312 terminates in coupler 314. Coupler 310 is adapted to cooperate with input connector 304 and coupler 314 is adapted to cooperate with output connector 306. Input shell 300 carries an "O"-ring 316 in a groove 318, therein. Output shell 302 has a groove 320 therein sized and shaped to receive, snugly, "O"-ring 316, whereby, a frictional engagement exists between shells 300 and 302 and they may be rotated with respect to each other and their relative positions will be fixed when rotation is completed.

Aperture 322 in input shell 300 has its center line 324 displaced in a first direction by a distance D-1 off of the axis of rotation 328 of shells 300 and 302. Aperture 330 in output shell 302 has its center line 332 displaced a distance D-2 off of axis of rotation 328 in a direction opposite to that in which center line 324 is displaced. The total mis-alignment of apertures 322 and 332 is the distance D-3. This condition produces maximum attenuation by attenuator 24 of the light input from optical fiber 308. Because of the eccentric locations of apertures 322 and 332, as relative rotation occurs between shells 300 and 302 apertures 322 and 332 go from a condition of maximum mis-alignment to one of maximum alignment, which is the condition for minimum attenuation of light passing thru attenuator 24. A 180 degree relative rotation produces the change from maximum to minimum attenuation. Grooves 334 permit adjustment of attenuator 24 by means of a screwdriver. The path thru the attenuator is an air path.

The advantage of this attenuator over others is that there is no additional air/glass interface nor intervening material that has a different transmission band to taint or color the optical signal. When using the attenuator at a point where a coupler is required anyway, there is little cost increase. Further, trying to match the signal strength of two optical fibers, the attenuation can be varied from the same minimum insertion loss that the connector would have to full attenuation without having to worry about spectral distortion.

The attenuation produced by this principle is more severe than other methods for the same levels of displacement. It is therefore only suitable for large core fibers. However, when smaller core fibers are used, a micro-lens can be used to expand the optical signal cross-section and the same principle applied. The signal is affected by the significant transmission band of the micro-lens, but in most applications this is not a significant factor.

Thus there has been provided a spectrometer or analyzer which is microprocessor-controllable with a chassis that can accept up to nine optical input cards. Each input card can be configured differently, perhaps looking for different component concentrations in a speciment and, perhaps, at the same time analyzing the color and texture of the product. The optical bench, which is the significant part of the system, is carried on an input card. A spectrometer according to this invention may be used to analyze multiple samples in rapid sequence with those samples being located remotely and, perhaps, in hostile environments. As a matter of precaution, it should be noted that special care is required in the selection of optical fiber cables to assure that the fibers contain few impurities that absorb light at the wavelengths of interest. For example, moisture or water measurements require that the optical fibers have a low hydroxyl concentration, a common impurity in most optical fibers. Each application requires analysis to determine the maximum cabling length. These distances vary with the application and with the operational wavelength. They can be as little as one or two meters or as great as several kilometers. Loss factors in the optical fibers and detector technology are the primary limitations. Other than the losses in the optical fibers, detector technology is the most critical factor in system performance. In the near infrared from 1 to 3 microns, Lead Sulfide photoconductors are preferred. From 3 to 5.5 microns, Lead Selenide conductors are used. Both of these detectors require similar electric coolers to reduce their thermal noise. The typical element operating temperature is minus 30 degrees C which is easily obtainable with a two-stage cooler, such as the combination of cooling elements 60, 61 in FIG. 1. Above 5.5 microns, the detector technology is limited because cryogenic cooling is not contemplated in this particular embodiment. Certain applications can utilize tailored Mercury-Cadmium Telluride photoconductors with thermoelectric coolers for measurements up to about 8 microns. Most detectors require a chopped optical input. This reduces 1/f noise in the detector. Additionally, photoconductive detectors have a non-zero dark current that needs to be measured and subsequently subtracted from all the other measurements. The blank positions (B) of fiber termination assemblies 40 and 114 provide this dark current measurement capability. The chopping frequency is chosen to optimize the detector's response and typically varies from 300–800 Hz.

In FIGS. 9(a) and 9(b) optical attenuator 24 includes input shell 300 and output shell 302. Input shell 300 includes threaded input connector 304 and output shell 302 includes threaded output connector 306. Incoming optical fiber 308 terminates in coupler 310 and output optical fiber 312 terminates in coupler 314. Coupler 310 is adapted to cooperate with input connector 304 and coupler 314 is adapted to cooperate with output connector 306. Input shell 300 carries an "O"-ring 316 in a groove 318, therein. Output shell 302 has a groove 320 therein sized and shaped to receive, snugly, "O"-ring 316, whereby, a frictional engagement exists between shells 300 and 302 and they may be rotated with respect to each other and their relative positions will be fixed when rotation is completed.

Aperture 322 in input shell 300 has its center line 324 displaced in a first direction by a distance D-1 off of the axis of rotation 328 of shells 300 and 302. Aperture 330 has its center line 332 displaced a distance D-2 off of axis of rotation 328 in a direction opposite to that in which center line 324 is displaced. The total mis-alignment of apertures 322 and 332 is the distance D-3. This condition produces maximum attenuation of the light input from optical fiber 308 by attenuator 24. Because of the eccentric locations of apertures 322 and 332, as relative rotation occurs between shells 300 and 302 apertures 322 and 332 go from a condition of maximum mis-alignment to one of maximum alignment, which is the condition for minimum attenuation of light passing thru attenuator 24. A relative rotation of 180 degrees produces the change from maximum to minimum attenuation. Grooves 334 permit adjustment of attenuator 24 by means of a screwdriver. The path thru the attenuator is an air path.

The advantage of this attenuator over others is that there is no additional air/glass interface nor intervening material that has a different transmission band to taint or color the optical signal. When using the attenuator at a point where a coupler is required anyway, there is a little cost increase. Further, when trying to match the signal strength of two optical fibers, the attenuation can be varied from the same minimum insertion loss that the connector would have to full attenuation without having to worry about spectral distortion.

The attenuation produced by this principle is more severe than other methods for the same levels of displacement. It is therefore only suitable for large core fibers. However, when smaller core fibers are used, a micro-lens can be used to expand the optical signal cross-section and the same principle applied. The signal is affected by the transmission band of the micro-lens, but in most applications this is not a significant factor.

The design of the spectrometer according to this invention utilizes an open architecture; that is, functions can be easily added or subtracted by card changes or program changes. The electrical bus 50 that the input cards plug into, is built to the VME bus standard (IEEE P1014). Any other cards built to this standard can also be interfaced. This allows marketplace competition to establish pricing of boards giving the desired functions. VME bus is the most popular bus architecture in Europe and the fastest growing in the United States. Some of the available boards that can be obtained as options for the analyzer are;

Analog input and output
Digital input and output
Serial communication ports
Parallel communications ports
Data storage units (disks or tape)
Graphic display generators
Redundant processors and memory
Communication nodes (Local area networks, e.g. MAP)
Display and data entry units Like the hardware, the software is modular and functions can be added. Typical functions include:

Additional calculations and data manipulations
Closed-loop control (PID and self-tuning algorithms)
Communications protocols to host computers
Complete process unit control and data acquisition
Accounting and custody transfer recording
Operator interface software The versatility of this system is truly open-ended. It is limited only by application and the implementer. Only minor adaptations are required to perform many different spectrometric functions in the same chassis. With this invention, four or more channels can cost less than the single channel units of the prior art.

While particular embodiments have been shown and described it will be apparent to those skilled in the art that variations and modifications may be made in those embodiments without departing from the spirit and scope of this invention. It is the purpose of the next claims to cover all such variations and modifications, as well as the primary embodiments set forth herein.

I claim:

1. A spectrometer for semi-simultaneous remote analyses of multiple samples, including:
   a sensing head, said sensing head including a source of broadband light, which light is continuous during operation of the spectrometer;
   a mechanically-driven optical multiplexer remote from said sensing head and coupled thereto by multiple pairs of optical fibers, each such pair including a reference-signal fiber and a measurement-signal fiber;

said optical multiplexer including stationary means for terminating said multiple pairs of optical fibers in circularly-disposed, spaced positions, and rotatable chopper means coaxial with said stationary means, said chopper means including a disk having a plurality of spaced light transmitting openings therein positioned to align sequentially, during rotation of said chopper means, with said fiber-optic means in said stationary means, each of said light transmitting openings carrying an interference filter set at a predetermined light wavelength;

a unitary opto-electrical transducer optically coupled to said chopper means for receiving light passing through said interference filter carried by each of said light transmitting openings in said chopper means; and, processing means including memory means for storing output signals from said opto-electrical transducer.

2. Apparatus according to claim 1 in which said fiber-optic means are spaced at first angle from each other along a common circle except as between two thereof which are spaced by an angular distance twice said first angle.

3. Apparatus according to claim 1 in which said chopper means includes, in addition, commutating means, said commutating means including multiple, evenly-angularly displaced reflective strips located proximate to the perimeter of said commutating means.

4. Apparatus according to claim 1 in which said chopper means includes, in addition, commutating means, said commutating means including multiple, evenly-angularly displaced reflective synchronizing strips and a reflective indexing strip, all located proximate to the periphery of said commutating means; and, opto-electronic synchronizing-signal generating means and opto-electronic indexing signal generating means positioned proximate to said commutating means for producing synchronizing signals and indexing signals, respectively, upon relative rotation between said commutating means, on the one hand, and said synchronizing signal generating means and indexing-signal generating means, on the other hand.

5. Apparatus according to claim 4 in which said opto-electronic synchronizing-signal and indexing signal generating means comprises an LED light source and phototransistor.

6. Apparatus according to claim 1 in which the number of light transmitting openings in said chopper means is two and they are spaced along a diameter of said chopper means.

7. Apparatus according to claim 1 in which the number of light transmitting openings in said chopper means is four spaced, angularly, 90 degrees from each other along a common circle.

8. Apparatus according to claim 1 in which said opto-electrical transducer is thermo-electrically cooled.

9. Apparatus according to claim 1 in which said processing means includes a variable-gain amplifier and attenuator.

10. For a spectrometer, an optical bench including;

stationary means for terminating multiple optical fibers in circularly-disposed, spaced positions, said optical fibers being displaced by a first angle from each other along a common circle except as between two thereof which are displaced by an angular distance along said same common circle which is twice said first angle;

a rotatable, disk-like chopper positioned coaxially with and proximate to said stationary means, said chopper including a plurality of spaced light-transmitting openings therein positioned to align sequentially, during rotation of said chopper, with said optical fibers in said stationary means, each of said light-transmitting openings including an interference filter set at a predetermined wavelength; and, a plano-convex lens, carried by said chopper and optically coupled to said interference filters on the surface of said chopper remote from said stationary means.

* * * * *